United States Patent [19]
Hilal et al.

[11] Patent Number: 5,344,420
[45] Date of Patent: Sep. 6, 1994

[54] SURGICAL TROCAR

[75] Inventors: Nabil Hilal, Mission Viejo; Said S. Hilal, Laguna Niguel, both of Calif.

[73] Assignee: Applied Medical Resources Corporation, Laguna Hills, Calif.

[21] Appl. No.: 152,242

[22] Filed: Nov. 12, 1993

Related U.S. Application Data

[63] Continuation of Ser. No. 791,878, Nov. 13, 1991, abandoned, which is a continuation-in-part of Ser. No. 654,815, Feb. 13, 1991, abandoned.

[51] Int. Cl.$^5$ .............................................. A61B 17/32
[52] U.S. Cl. ........................................ 606/28; 606/16; 606/42; 606/45; 604/164
[58] Field of Search ............... 606/181, 184, 7, 12, 606/13, 14, 15, 27, 28, 32, 41, 42, 45, 50, 29, 48; 604/164

[56] References Cited

U.S. PATENT DOCUMENTS

| | | | |
|---|---|---|---|
| 1,741,461 | 12/1929 | Herman | 606/45 |
| 3,595,239 | 7/1971 | Petersen | 606/45 |
| 4,043,342 | 8/1977 | Morrison, Jr. | 606/48 |
| 4,418,692 | 12/1983 | Guay | 606/45 X |
| 4,750,489 | 6/1988 | Berkman | 606/181 X |
| 4,807,620 | 2/1989 | Strul et al. | 606/28 |
| 4,850,353 | 7/1989 | Stasz et al. | 606/45 |
| 4,986,814 | 1/1991 | Burney et al. | 604/264 X |
| 5,057,099 | 10/1991 | Rink | 606/12 |
| 5,071,222 | 12/1991 | Laakman et al. | 606/28 X |

*Primary Examiner*—Peter A. Aschenbrenner
*Attorney, Agent, or Firm*—Richard L. Myers

[57] ABSTRACT

A surgical trocar includes an operative sleeve adapted for disposition across a tissue barrier and an obturator removably disposed in the sleeve. A source of energy is introduced to a cutting element disposed at the distal end of the obturator for energizing the cutting element to cut tissue barrier. The distal end of the obturator and the distal end of the operative sleeve can be advanced through the cut tissue and the obturator removed leaving the sleeve operatively disposed for further surgery.

37 Claims, 5 Drawing Sheets

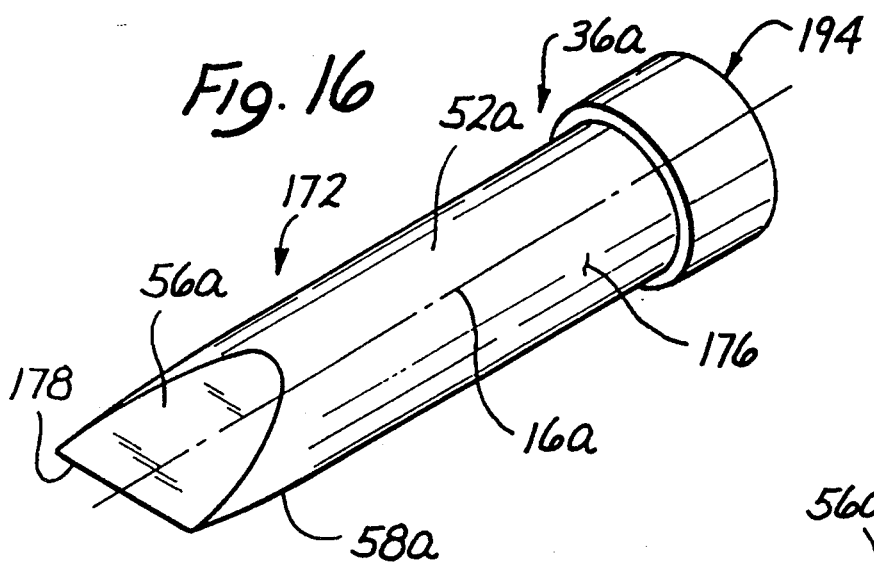
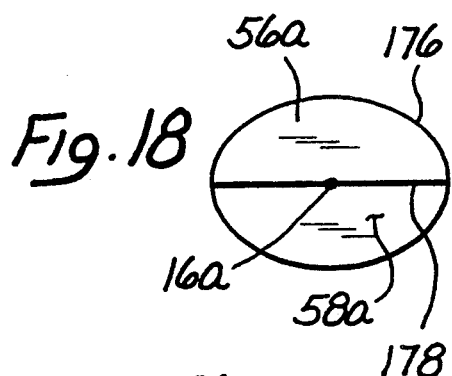
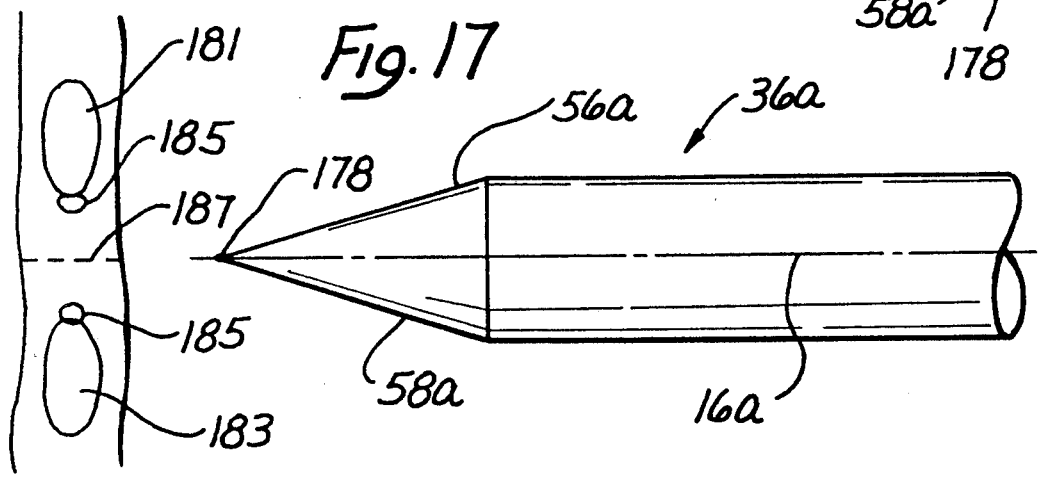
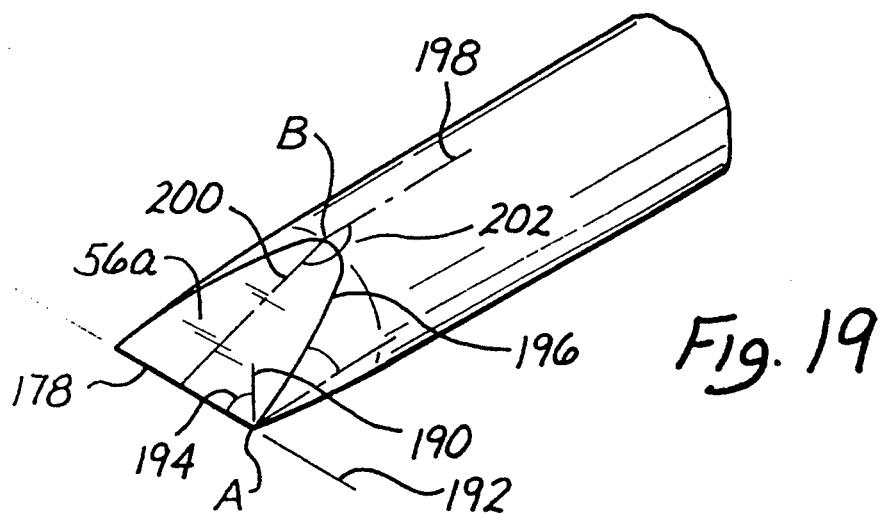

SURGICAL TROCAR

This application is a continuation of application Ser. No. 07/791,878, filed Nov. 13, 1991, now abandoned which is a continuation-in-part of U.S. patent application Ser. No. 07/654,815, filed on Feb. 13, 1991 by Hilal, et al. and entitled Surgical Trocar, now abandoned.

BACKGROUND OF THE INVENTION

Devices and procedures for providing an enlarged tubular access into a body cavity or body conduit, were first conceived when catheters became particularly valuable for noninvasive surgery. A catheter which may have had a diameter of such as 5 French is typically very flexible and therefore does not have the column strength necessary to puncture the skin or a vessel in order to accommodate insertion of the catheter. A method which is still the preferred procedure was developed whereby a common surgical needle is inserted through the skin and into the vessel. This needle was closely overlaid with a thin sheath, commonly referred to as an introducer, which is carried by the needle into the vessel. When the needle was removed, the introducer was left in place and provided the tubular access through which the catheter could then be inserted.

In more recent times, noninvasive surgery has further advanced so that large body cavities such as the abdomen can be accessed through tubular devices and the surgical procedures performed with long narrow instruments through those access devices. It is not surprising that these devices, commonly referred to as trocars, are introduced through the abdominal wall or other tissue barrier, in much the same manner as that employed by the catheter introducer systems. Thus, trocars typically include a puncturing device, commonly referred to as an obturator, and a closely spaced outer sheath or cannula. In this case the obturator may have an outside diameter such as 10 millimeters, where the cannula has a similar inside diameter. Once the cannula is in place, narrow surgical apparatus can be inserted through the cannula to perform common functions such as cutting, irrigating, aspirating, grinding, traction and removal of body parts.

While the above mentioned procedure for introducing catheters has remained satisfactory, this same procedure applied to trocars has not been effective for two primary reasons. First, the size of the required puncture is much larger than that associated with catheters. Second, the abdominal wall consists of a material having a much greater density than merely skin or vessel walls. The puncture required for a trocar must typically be made through muscle which provides a much higher resistance to entry. As a result of these two differences, forces as great as 100 pounds may be required to insert a trocar into a body cavity.

In order to accommodate forces of this magnitude, obturators have been formed from solid metal rods and provided with very sharp points and long cutting edges leading from the point to the outer circumference of the obturator. While this has had some effect on the force required for insertion, it has only aggravated the problem associated with the presence of organs in close proximity to the abdominal wall.

In order to avoid puncturing of these organs, it has been necessary to stop the forward movement of the trocar immediately upon penetration. Thus the procedure has called for a tremendous force in order to penetrate the abdominal muscle and an immediate stopping of that force at the point where there is no further resistance to forward movement. In some cases, physicians have attempted to avoid the significant forward pressure by twisting and turning the trocar. This has tended to significantly traumatize the incision.

More recently, attempts have been made to mechanically cover the sharp cutting tip and edges immediately following penetration. U.S. Pat. No. 4,654,030 discloses a sheath which is biased to move forwardly over the point of the trocar as soon as it penetrates the abdominal wall. Elaborate apparatus for biasing this sheath to the forward position have been complicated by requirements for a long throwing distance and a short throwing time.

The need has remained for an apparatus and method which can easily puncture (with a low force and providing a high degree of control) along a precise incision (providing low trauma and excellent healing characteristics) while avoiding any further cutting immediately following penetration.

SUMMARY OF THE INVENTION

These features are provided in accordance with the present invention which applies electrocautery techniques in the formation of a puncture wherein a long instrument, such as a trocar, can be advanced substantially perpendicular to the wall of a cavity, such as the abdominal wall. An electrocautery element such as a wire or blade can be provided at the distal end of the trocar and operated in accordance with monopolar or bipolar techniques to cut the abdominal wall as the trocar is advanced. Means can be provided for controlling the shape of the electrocautery element at the distal end of the trocar in order to vary the shape, for example the width, of the incision.

Apparatus for covering or retracting the electrocautery element immediately upon penetration of the wall is desirable to avoid cutting any proximate organs. This apparatus might include a pressure transducer responsive to the absence of pressure beyond the abdominal wall, or a logic circuit with properties for detecting a sharp reduction of cutting current upon penetration of the wall.

In one aspect of the invention, a surgical trocar assembly is provided for penetrating a barrier of tissue and providing an operative channel through the tissue barrier into a body cavity. The assembly includes an operative sleeve and an obturator removably disposed in the sleeve and extending beyond the distal end of the sleeve. A cutting element is disposed at the distal end of the obturator and adapted to be moved into contact with the tissue. Means is provided for conducting energy from a source to the cutting element and for energizing the cutting element to cut the tissue, whereby the distal end of the obturator and operative sleeve can be advanced through the cut tissue and across the tissue barrier.

In another aspect of the invention, a surgical apparatus is adapted for creating an incision through a tissue barrier. The apparatus includes a rod having walls disposed along a longitudinal axis and narrowing to form an apex at the distal end of the rod. Portions of the walls define a slot extending along a plane including the axis of the rod and means is disposed in the slot for conducting electrical energy toward the distal end of the rod. Means for energizing the conducting means facilitates cutting the tissue with the rod when the rod is placed in proximity to the tissue and when the rod is moved through the cut tissue to create the incision.

A method for inserting the cannula through the wall of a body cavity includes the steps of inserting an energy conducting cutting device through the cannula; contacting the wall of the cavity with the cutting element, energizing the cutting element to cut the wall of the cavity; and advancing the tip of the cutting device to create an incision through the wall of the cavity.

These and other features and advantages associated with the present invention will be more apparent with a description of the preferred embodiments of the concept and reference to the associated drawings.

DESCRIPTION OF THE DRAWINGS

FIG. 16 is a perspective view of an obturator having a tip portion of particular interest to the present invention;

FIG. 17 is a side elevation view of the tip portion of the obturator illustrating its advantageous use in puncturing the abdominal cavity between a pair of ribs;

FIG. 18 is a front elevation view of the tip portion taken along lines 18—18 of FIG. 16; and FIG. 19 is an enlarged view of the tip portion illustrated in FIG. 16.

DESCRIPTION OF PREFERRED EMBODIMENTS

Figure 1:
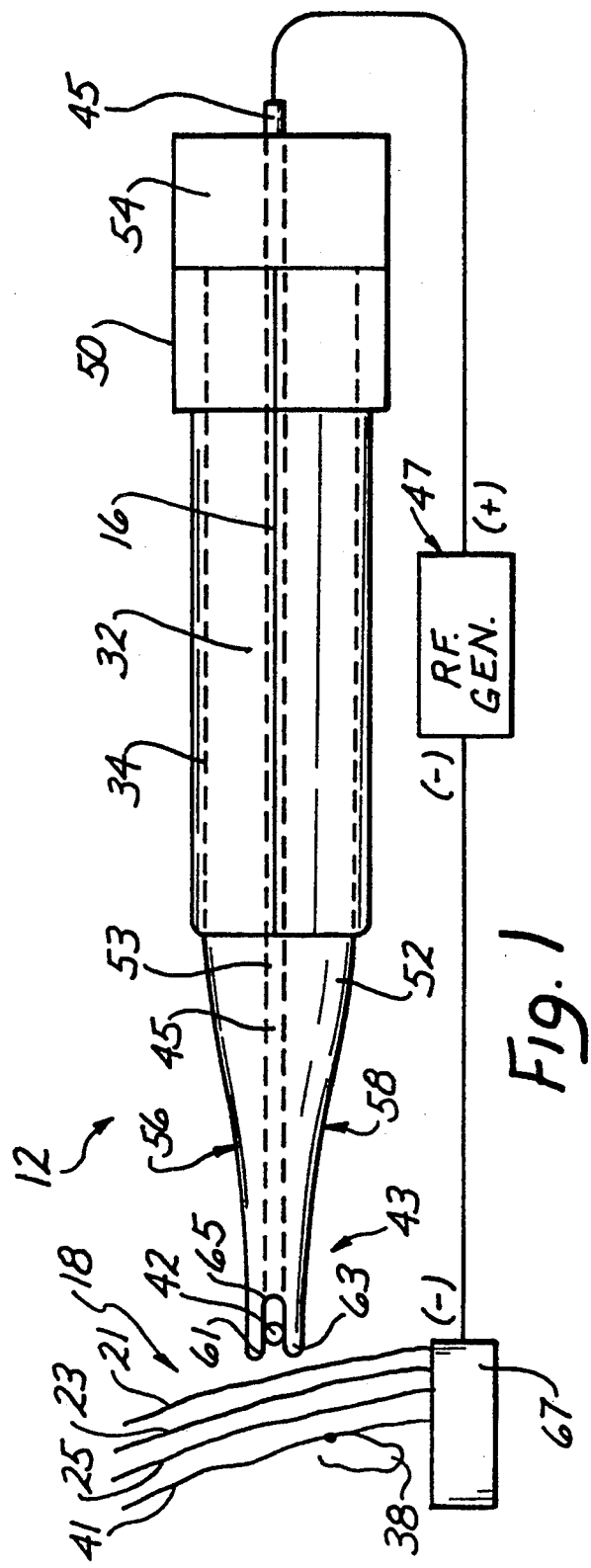
FIG. 1 is a side elevation view of one embodiment of the trocar associated with this invention operatively positioned to penetrate a tissue barrier.

A surgical trocar is illustrated in FIG. 1 and designated generally by the reference numeral 10. The trocar 10 is a narrow elongate instrument having a distal end 12 and a proximal end 14. It is typically configured along a longitudinal axis 16 and is generally circular in radial cross-section.

It is the purpose of the trocar 10 to provide a channel through a tissue barrier in order to provide access across the barrier into a body cavity. By way of example, an abdominal wall 18 is illustrated in FIG. 1 and typically includes a layer of skin 21, a layer of fat 23, and a layer of muscle 25 which form the tissue barrier to an abdominal cavity 27.

The trocar 10 typically includes an elongate tube or cannula 32 having a cylindrical configuration and a wall thickness such as 0.015 inches. The cannula 32 has an interior bore or channel which is typically in a range of diameters between 5 to 12 millimeters. It is the purpose of the trocar 10 to pierce, cut, incise or otherwise puncture the tissue barrier, such as the abdominal wall 18, and to leave the cannula 32 extending through that incision with the channel 34 providing an access port into the cavity 27. Through this channel 34, various surgical instruments such as cutters, clamps, traction devices, visualization devices, aspirators and irrigators can be positioned and manipulated to perform a particular surgical procedure within the cavity 27.

The trocar 10 also includes an obturator which extends through the cannula 32 and provides the means for cutting through the wall 18 to provide for insertion of the cannula 32. In the past, obturators have been formed from solid metal rods which have been sharpened to a point at the distal end 12 of the trocar 10. The forces necessary to puncture the abdominal wall 18 with such a device have been considerable due primarily to the presence of the muscle layer 25 in the wall 18. Puncturing of the wall 18 with such devices has been further complicated with the close proximity of important organs such as the liner 38 which, in some patients may actually be attached to the abdominal wall 18 by an adhesion 41. In order to avoid puncturing these organs, it has been an absolute requirement that the forward movement of the trocar 10 be stopped as soon as the distal tip of the obturator pierces through the interlayer of the wall 18. These conflicting requirements to provide a significant puncture force and then to immediately halt application of that force, have made the trocars of the past both difficult and dangerous to use.

In accordance with the present invention an obturator 36 includes a distal tip 43 which extends beyond the distal end of the cannula 32. This tip 43 is provided with at least one electrocautery wire 42 which can be activated through a conductor 45 by a radiofrequency generator 47.

Initially the trocar 10 is advanced until the wire 42 and the tip 43 are brought into contact with the tissue barrier such as the wall 18. Activating the wire 42 with radiofrequency energy causes the contacted cells to vaporize forming an opening or incision in the wall 18. With the application of a relatively minimal force, the trocar 10 can be advanced through the tip 45 clears the inner layer of the wall 18, such as the muscle layer 25. At this point, it is desirable to de-energize the cutting element or wire 42 so that any further forward movement of the trocar 10 does not accidently cut an interior organ such as the liner 38. Various apparatus and methods for sensing this particular location and inhibiting further cutting is discussed in greater detail below.

At the proximal end 14 of the trocar 10 the cannula 32 is attached to a valving mechanism 50 which can be of the type disclosed by Moll in U.S. Pat. No. 4,654,030, or disclosed by applicant in copending U.S. patent application Ser. No. 07/630,078 filed on Dec. 19, 1990.

The obturator 36 includes an elongate shaft 52 which may include interior portions defining an axial channel 53 for the conductor 45. This shaft 52 extends through the valving mechanism 50 as well as the cannula 32 with the tip 43 extending beyond the distal end of the cannula 32. A finger knob 54 can be attached to the shaft 52 of the obturator 36 to facilitate application of the minimal axial force required to advance the trocar 10. Upon penetration of the wall 18, this finger knob 54 can be withdrawn proximally through the cannula 32 and the valving mechanism 50. In this manner, the cannula 32 is left in place with the interior channel 34 providing access across the abdominal wall 18 into the body cavity 27.

In the illustrated embodiment, the distal tip 43 of the obturator 36 has the configuration of a duck bill. It is defined primarily by a pair of opposing ramps 56, 58 which extend from the outer surface of the shaft 52 inwardly with progressive distal positions along the ramps 56, 68. At the distal end of the obturator 36, the ramps 56 and 58 terminate in a pair of lips 61, 63 respectively which define an interior recess 65 that is configured to receive the wire 42.

It will be noted that the lips 61, 63 extend slightly distally of the wire 42 by a particular distance. As the trocar 10 is moved forwardly, these lips 61, 63 are the only part of the trocar 10 which actually touch the wall 18. This particular distance is carefully selected, however, so that when the lips 61, 63 touch the wall 18, the wire 42 is close enough to the wall 18 that the most proximate cells vaporize to create the desired incision. This cutting by close proximity is commonly referred to as arcing. As used herein the cutting element, such as the wire 42, is deemed to be in contact with the wall 18 if the desired arcing or cutting occurs.

In the embodiment of FIG. 1, the electrocautery technique is monopolar; that is, only a single pole, such as the positive pole, is carried by the trocar 10. In this type of technique, the patient is laid directly on a large plate which provides the second pole required by the electrocautery system. The RF generator 47 produces a radio frequency electrical energy signal which travels through the positive electrode connected to the wire 42 and through the body of the patient, to the negative pole at the plate 67. Where this conduction path is large in cross-section, the current density is very small. However, in proximity to the wire 42 the current path is very small in cross-section so the current density is quite large. It is this large current density which results in vaporizing the cells of the wall 18 in proximity to the wire 42.

Figure 3:
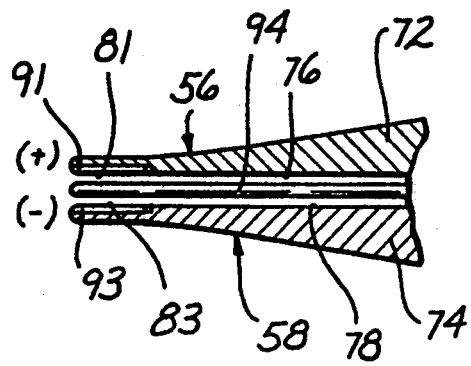
FIG. 3 is a side elevation view of the distal end of a further embodiment of the trocar.
Figure 4:
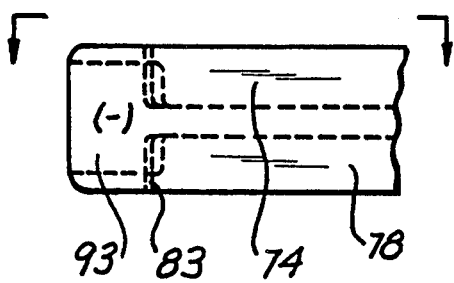
FIG. 4 is a cross-section view taken along lines 4—4 of FIG. 3.

It will be apparent that a bipolar electrocautery technique is equally applicable to this invention and may actually be preferred in some circumstances. A bipolar embodiment is illustrated in FIGS. 3 and 4 wherein the shaft 52 of the obturator 36 is separated axially into two half-shafts 72 and 74 each having an axial cross-section of a half circle and each including one of the duck bills associated with the nose 43. Each of the half-shafts 72, 74 has an inner surface which defines a recess near the associated tip 61, 63 respectively. For example, the half-shaft 72 includes an inner surface 76 which defines a recess 81 near the lip 61. Similarly, the half-shaft 74 has an inner surface 78 which defines a recess 83 near the lip 63.

These recess 81 and 83 are configured to receive a pair of blades 85, 87 respectively which are connected to the two electrical poles of the RF generator 47. Thus, the blade 85 is connected through a conductor 90 to the positive pole of the generator 47 while the blade 87 is connected through a conductor 92 to the negative pole of the generator 47. A layer of insulation 94 is sandwiched between the surfaces 76, 78 to separate the blades 91, 93. In this bipolar embodiment, current travels from the blade 91 through the tissue wall 18, around the insulator 94 and into the blade 93.

Figure 2:
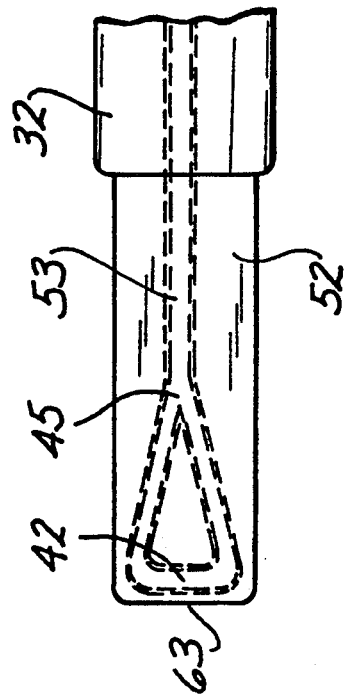
FIG. 2 is a top plan view of the trocar embodiment illustrated in FIG. 1.

The exact configuration of the cutting elements 42, 91 and 93 in these embodiment is not important as long as the desired current density can be maintained. Thus the wire 42 and the blades 91 and 93 may be interchangable in the FIG. 1 and FIG. 2 embodiments.

Figure 5:
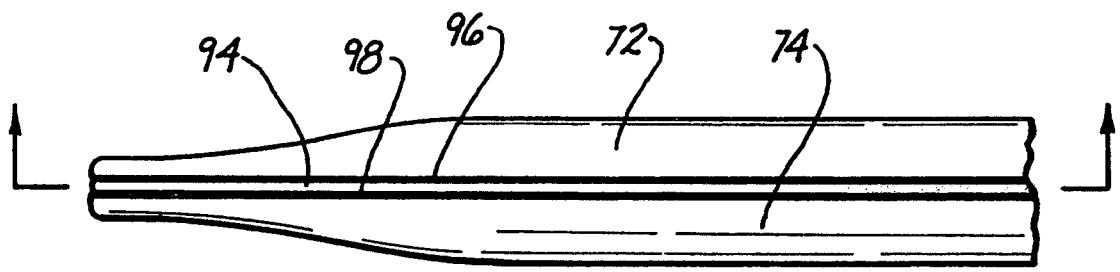
FIG. 5 is a side elevation view of a further embodiment of the trocar.
Figure 6:
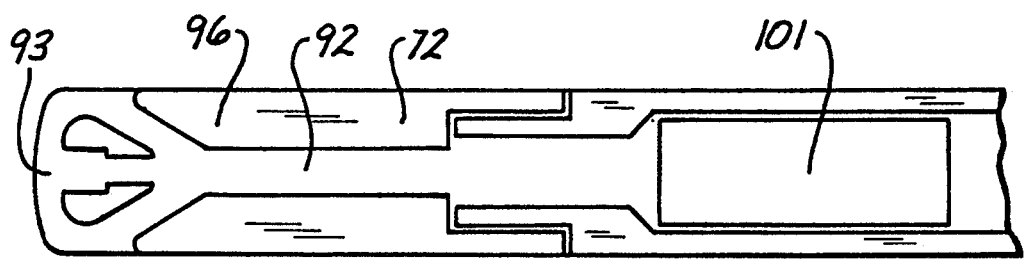
FIG. 6 is a cross-section view taken along lines 6—6 of FIG. 5.
Figure 8:
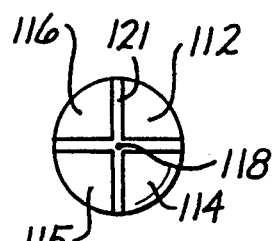
FIG. 8 is an end view of the embodiment illustrated in FIG. 7.
Figure 7:
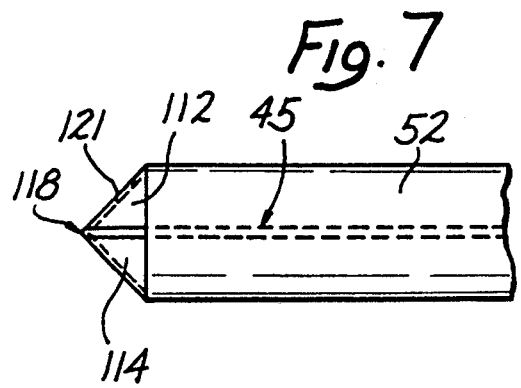
FIG. 7 is a side elevation view of a further embodiment of the trocar illustrating a plurality of wire cutting elements.

In a further embodiment of the invention illustrated in FIGS. 5 and 6, the shaft of the obturator 36 is again separated into the half-shafts 72 and 74. Along either or both of the interior surfaces 76, 78 a conducting material can be doped into or otherwise deposited on the material forming the half-shaft 72, 74. For example, in a preferred embodiment, the half-shafts 72, 74 are formed from glass or sintered ceramic and the layers 96, 98 contain a conductive polymer or metal which is doped into the surfaces 76, 78 respectively. In a monopolar embodiment, only one of the layers 96, 98 is required. In the bipolar embodiment illustrated both layers 96, 98 are required as well as the insulation layer 94 which separates the two half-shafts 72, 74.

In this particular embodiment, the doped layer, for example the layer 98, can form both the cutting element, such as the blade 93, as well as the associated conductor, such as the conductor 92. The layer 98 may also include a region of epitaxial layering which forms a logic circuit 101 discussed in greater detail below.

Other embodiments of the invention which take advantage of the electrocautery technique are illustrated in FIGS. 7 through 11. In the FIG. 7 embodiment, which is also shown in the end view of FIG. 8, the distal end of the obturator 36 is formed with three planes or lands 112, 114 and 116 which extend from the outer surface of the shaft 52 distally to a point 118. In this embodiment, a wire 121 is disposed along each of the lines defined by the intersection of the lands 112, 114 and 116. In operation, the wires 121 cut the tissue of the wall 18 along three lines so that the incision is defined by three flaps of the tissue. This particular embodiment may be desirable where it is necessary to equalize pressures of the tissue on the outer surface of the cannula 32.

Figure 9:
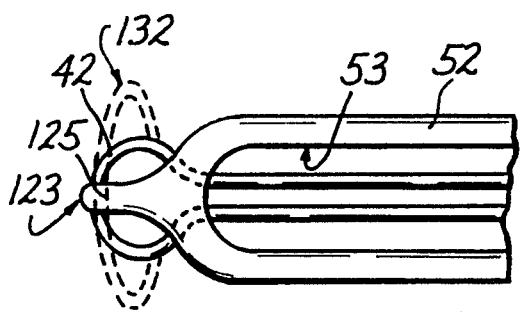
FIG. 9 is a side elevation view of still a further embodiment of the trocar with an expandable cutting element.

In the embodiment of FIG. 9, the distal end of the obturator 36 is formed with a projection 123 which extends distally and axially of the trocar 10. A recess or channel 125 is defined to extend generally radially across the projection 123. The cutting element or wire 142 in this embodiment passes down the axial channel 53 in the obturator 36 and passes outwardly of the shaft 52 through a port 127 at the distal end 12. The wire 42 then passes through the recess 125 in the projection 123 and back into the shaft 52 through a port 130.

This embodiment is of particular interest since either end of the wire 42 can be advanced distally within the axial channel 53 to expand the width of the wire 42 at the distal end of the trocar 10. In fact, both ends of the wire 42 can be moved distally to extend the exterior portions of the wire 42, for example to the dotted position 132 illustrated in FIG. 6. This position 132 has a significantly greater width and therefore provides a wider incision in the wall 18. Thus the wire 42 can be advanced and retracted within the axial channel 53 to vary the size and shape of the resulting incision.

Figure 10:
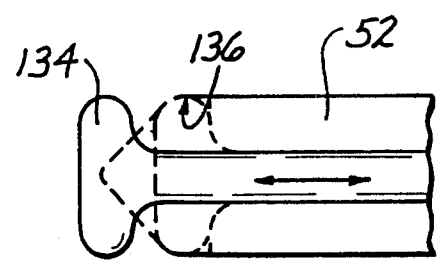
FIG. 10 is a top plan view of a further embodiment of a trocar with a retractable cutting element.
Figure 11:
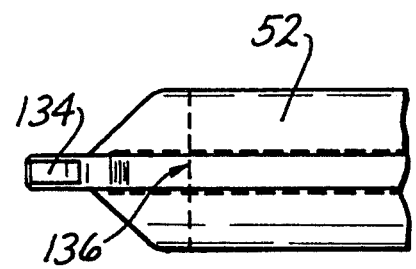
FIG. 11 is a side elevation view of the embodiment illustrated in FIG. 10.

In the embodiment of FIGS. 10, 11, the cutting element has the configuration of a blade 134 similar to that first discussed with reference to FIG. 3. In this case, the blade 134 can be advanced beyond the distal end of the shaft 52 associated with the obturator 36. It can also be retracted into a recess 136 in the shaft 52 in order to inhibit any further cutting of the tissue associated with the wall 18.

Figure 12:
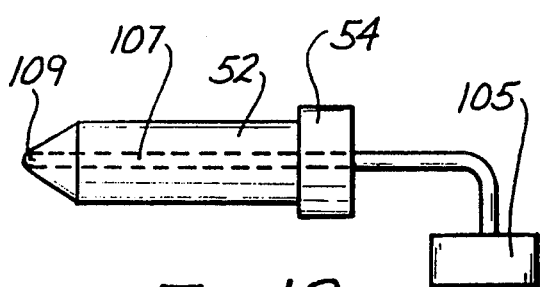
FIG. 12 is a schematic view of a trocar using an optical cutting system including a laser.

The invention is not limited to the electrocautery embodiments or techniques disclosed above. Rather, other types of cutting elements can be disposed at the distal end of the obturator 36 to increase the cutting capabilities of the trocar 10. One such embodiment is illustrated in FIG. 12 which provides for optical cutting in combination with a laser 105. The optical energy provided by the laser 105 is conducted through an optical fiber 107 to a cutting element or lens 109 which concentrates the energy to form the required incision in the wall 18.

It will be apparent to those skilled in the art that ultrasonic cutting is equally applicable to the present invention. In such a device, the conductor would transmit energy not in the radiofrequency range but rather in the ultrasonic range between 100 KHz and 1.2 MHz. As this energy emanates from the cutting element at the distal end of the trocar 10, the energy can be focused to activate the proximate cells and cause those cells to vaporize. Thus the ultrasonic cutter would function much as a microwave. One advantage of this system is that ultrasonic cutting does not require the two electrical poles associated with both monopolar and bipolar radiofrequency cutting. Focusing of the ultrasonic energy could be achieved with suitable wave guides.

One of the most significant problems confronting trocar procedures of the past has been associated with the need to compromise two conflicting requirements: 1) the requirement to provide a significant axial pressure to force the trocar 10 through the wall 18; and 2) the need to immediately cease application of that significant force upon penetration of the wall 18. Attempts have been made to address this problem automatically and mechanically with the provision of a protective sheath armed in a rearward position but bias to spring to a distal position covering the distal tip of the obturator 36 upon penetration of the wall 18.

This attempt to avoid relying totally on the surgeon for both of the conflicting requirements has met with only limited success. Since the protective sheath has necessarily been larger than the diameter of the obturator 36, the distal end 12 if the trocar has been required to move beyond the point of penetration in order to clear the distal end of the shield. In an attempt to provide reduced insertion forces, the angle between the axis 16 and the lands 112, 114, and 116 has been reduced. While this has decreased the angle of inclination associated with these lands 112, 114, and 116, it is also extended the length of the lands 112, 114, and 116 rearwardly along the shaft 52. This is necessarily required that the protective sheath be thrown a greater distance in order to cover the point 118 of the obturator 36. The critical timing of this sheath response has not been sufficient to avoid the dramatic consequences associated with interior cutting.

Building on the advantages associated with the present invention whereby cutting by the obturator 36 is accomplished with electrical or optical energy, means can now be provided to sense complete penetration of the wall 18 and to cease further cutting by the cutting element.

Figure 13:
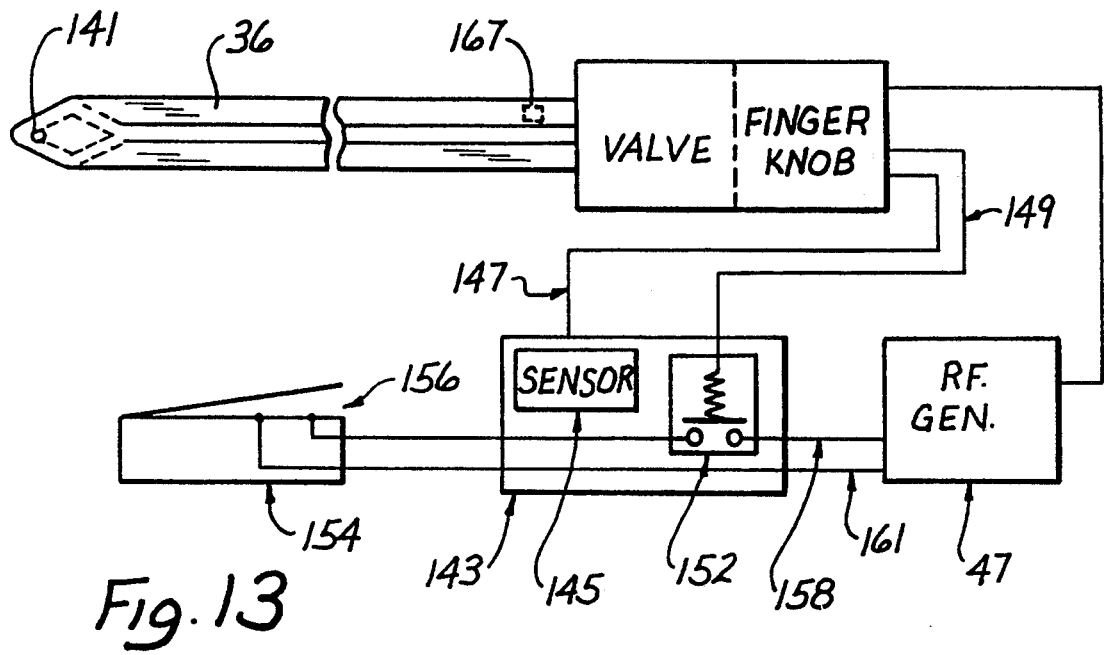
FIG. 13 is a schematic view of a preferred embodiment for sensing penetration of the tissue barrier.
Figure 14:
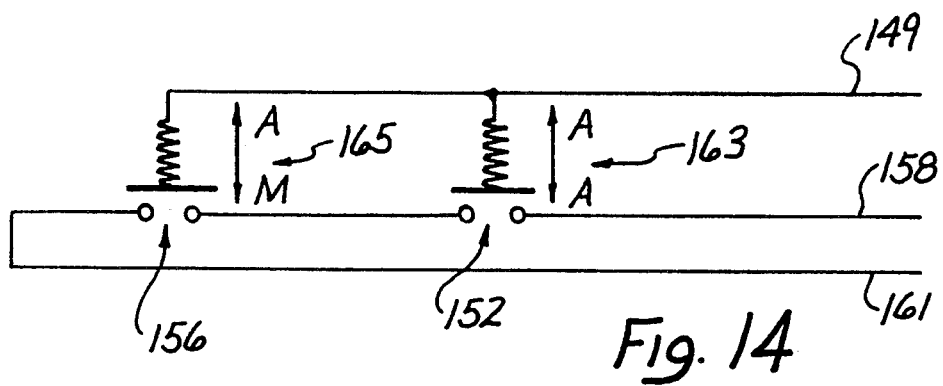
FIG. 14 is a schematic view of a switch system including an automatic switch and a manual override.

With reference to FIG. 13, a particular embodiment of the obturator 36 may include means disposed near the distal end 12 of the trocar 10 for sensing penetration of the wall 18 by the obturator 36. The sensor 141 will typically be connected to a penetration detection and response circuit 143 which controls the RF generator through a pair of conductors 158, 161. In the illustrated embodiment, the current 143 includes an energy source 145 for energizing the sensor 141 through one or more conductors 147.

Upon penetration of the wall 18, the sensor 141 provides signal characteristics on a conductor 149. In a particular embodiment, a switch 152 can be included in the response circuit 143 and provided with characteristics responsive to the signal on the conductor 149 to deactivate the generator 47. Thus the switch 52 has characteristics for closing when the sensor 141 is in proximity to the tissue and for automatically opening when the sensor 141 detects penetration of the wall 18. This switch 152 can be interposed in series with a foot pedal 154 which includes a manual switch 156 for providing continuity between the two conductors 158, 161 which activate the generator 47.

Under certain circumstances, it may be possible that the sensor 141 would detect the absence of pressure if the physician merely discontinues forward movement of the trocar 10 through the wall 18. Under these circumstances, a physician might decide to proceed with further cutting and therefore desire that the RF generator 47 be reactivated. This can be easily accomplished by a circuit 143 which is responsive to further pressure on the sensor 141 to close the switch 152. However, in a particular embodiment, it may be desirable to provide lock-out characteristics which require some manual switching by the physician in order to reactivate the generator 47. Such a circuit is illustrated schematically in FIG. 9 wherein the switches 152 and 156 are both responsive to the signal characteristics on conductor 149 to automatically open when the sensor 141 indicates that the wall 18 has been penetrated.

If additional pressure is detected by the sensor 141, the switch 152 would automatically close as illustrated by the arrow 163. However, the switch 156 would require manual closure by the physician as illustrated by the arrow 165.

In other embodiments, the sensor 141 could be a responsive to the presence or the pressure of insufflation gasses which are commonly used to inflate the abdominal cavity 27. These gases would be sensed only on the interior side of the wall 18 so the sensor 141 would actually be detecting penetration of the wall 18 by the obturator 36. These gas pressures could also be sensed in an embodiment providing for a longitudinal channel, such as the axial channel 53, which could convey the pressures to the sensor 141 at a more proximal location such as that illustrated at the dotted position 167 in FIG. 13.

Figure 15:
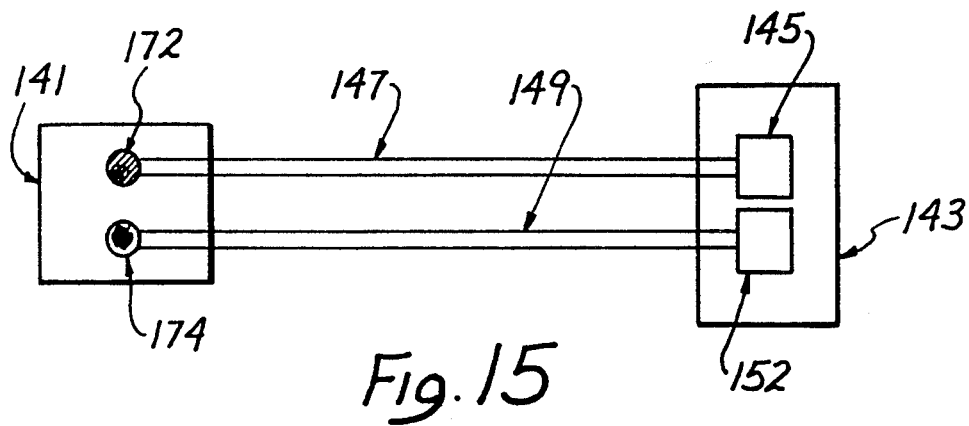
FIG. 15 is a schematic view of a infrared system for detecting penetration of the tissue barrier.

In still a further embodiment, the sensor 141 could be an infrared sensor including an LED 172 activated by the energizer 145 and a detector 174 providing the switch 152 with signal characteristics on the conductor 149. Such an IR sensor 141 as illustrated in FIG. 15 would sense the proximity of tissue by the reflectance of light from the LED 172 to the detector 174.

Another way of sensing penetration of the wall 18 is particularly adapted for the embodiment illustrated in FIGS. 5 and 6. In this case, the logic circuit 101 provides means for sensing changing electrical characteristics in proximity to the cutting element, such as the blade 93. These electrical characteristics may include capacitance, resistance, current magnitude, current density, or any combination thereof. These characteristic will tend to vary most dramatically as the blade 93 approaches the interior surface if the wall 18. As the tissue surrounding the blade 92 is reduced in thickness, the resistance to current flow will rise. Not only will the magnitude of the current in conductor 92 decrease, but the density of the current passing through the tissue will also tend to decrease. Any one or all of these characteristics can be detected by the logic circuit 101 to provide a means for inhibiting further cutting of tissue upon complete penetration of the wall 18.

The configuration of the distal tip of the trocar 10 as illustrated in FIG. 1 is of particular interest not only to an electrosurgical trocar but also to mechanical trocars. This tip is discussed more specifically with reference to FIGS. 16–19. In these figures, structures which are similar to those previously discussed are referred to with the same reference numerals followed by the lower case letter "a".

In FIG. 16, the obturator 36a is a mechanical obturator adapted for use with a trocar system which cuts tissue with the application of force on a sharp edge of the instrument. The obturator 36a includes a shaft 52a extending along a longitudinal axis 16a between a tip portion 172 at its distal end and a handle portion 174 at its proximal end. The shaft 52a in a preferred embodiment has a generally cylindrical surface 176. The handle portion 174 includes the finger knob or handle 54a.

The distal portion 172 of the shaft 52a is formed from a pair of opposing ramps or surfaces 56a and 58a. These surfaces converge distally and intersect each other at a line 178 which is disposed at the distal end of the tip portion 172. In a preferred embodiment, the surfaces 56a and 58a are planar in configuration to facilitate manufacture of the device. In other embodiments these surfaces may be more rounded as illustrated in FIG. 1.

The surfaces 56a and 58a are disposed at a relative angle preferably in a range between 15° and 45°. A smaller angle facilitates penetration of the tissue while a larger angle reduces the length of the tip portion 172. In a preferred embodiment, the relative angle between the surfaces 56a and 58a is about 30°. This relative angle between the surfaces 56a and 58a can be divided equally by the axis 16a, or alternatively, the surfaces 56a and 58a may have different angles with respect to the axis 16a.

In the illustrated embodiment, the line 178 at the intersection of the surfaces 56a and 58a passes through the axis 16a of the shaft 52a. Preferably the axis 16a is generally perpendicular to the line 178 and bisects the line 178. In this embodiment, the line 178 has a length which is generally equivalent to the diameter of the shaft 52a.

This configuration for the tip portion 172 is particularly desirable when the obturator 136a is used to puncture the abdominal wall 18a between a pair of ribs 181, 183. Blood vessels 185 are often present in this region along with various ligaments and other elements of tissue which should not be cut.

The wedge configuration of the tip portion 172 enables the obturator 36a to be inserted between the ribs 181, 183 without exposing the vessels 185 to any sharp cutting edge. Furthermore, the opposing surfaces 56a and 58a act to diametrically separate the ribs 181, 183 so that the only cutting occurs along a plane 187 illustrated by a dotted line which extends perpendicular to the abdominal wall 18a and intermediate the ribs 181, 183.

It is of particular interest to note that the outer surface 176 of the shaft 52a intersects each of the ramps or surfaces 56a, 58a at an obtuse angle between 90° and 180°. Referring to the enlarged view of FIG. 19 one can see that a point A is defined by the intersection of the surfaces 56a, 58a and 176. At this point A, the surface 176 is generally vertical as shown by the axis 190. The surface 56a is horizontal as shown by the axis 192. It follows that an angle 194 defined by the intersection of these surfaces 56a and 176 is about 90° at the point A.

As the surface 56a moves proximally, its intersection with the surface 176 of the shaft 52a follows generally along a line 196. From the point A, the line 196 travels proximally and then increasingly radially with progressive positions in the proximal direction. At a point B where the surface 56a intersects the surface 76 at its most proximal position, the line 196 extends only radially. At this point B, the surface 176 extends generally horizontally as shown by an axis 198. The surface 56a extends almost horizontally along an axis 200. An angle 202 which exists between an axis 198 and the axis 200 approaches 180°. In a preferred embodiment wherein the surface 56a has an angle of 15° with respect to the axis 16a, the angle 202 is 165°.

It follows that between the points A and B, the angle between the surface 56a and the surface 176 is an obtuse angle which varies generally from 90° to 180°. Since this is an obtuse angle, the line 196 is not particularly sharp and therefore is less likely to produce a cutting action. To further inhibit any cutting action along the line 196, this line of intersection can be rounded to further reduce its sharpness.

Although the embodiments of FIGS. 16–19 are directed primarily to a mechanical obturator 36a, it will be apparent that the advantages associated with the tip portion 172 are equally valuable with respect to an electrosurgical trocar. In such an embodiment, the electrosurgical electrode or wire 42 would be disposed along the line 178.

Under certain circumstance it may be desirable to view the distal end of the obturator 36a as cutting occurs. Such a viewing mechanism might take the form of a fiber optic cable 204 terminating at a wide angle lens 206 as illustrated in FIG. 16. The viewing mechanism would not only be beneficial in monitoring the cutting of the tissue, but could also provide information as to the nature of the tissue being cut. This would be of particular importance when the obturator 36a fully penetrates the wall 18. As noted, it is important to immediately cease cutting at this point of penetration in order to avoid any damage to interior organs.

Although this invention has been discussed with reference to various electrical and optical cutting circuits and exemplary switching circuits, it will be apparent to those skilled in the art that the invention can be otherwise embodied. Generally, any energy source can be coupled to the distal end of the obturator 36 and its energy converted into forms suitable for cutting tissue. Various cutting elements and cutting element configurations will be apparent depending on the nature of the energy provided. Various types of technology can also be incorporated into the sensor 141 all with the intent to provide some measurable indication at the point in time when the obturator 36 penetrates the wall 18.

Due to the broad nature of this invention, the breadth of the associated concept should not be limited merely to the disclosed embodiments or the drawings, but should be determined only with reference to the following claims.

We claim:

1. A medical device for providing access across a body wall into a body cavity, comprising:
    means for creating a hole through the body wall;
    an elongate shaft included in the hole creating means and extending between a tip portion at a distal end of the shaft and a handle portion at a proximate end of the shaft, the shaft having an outer surface;
    the tip portion of the shaft defined by a pair of surfaces each intersecting the outer surface of the shaft, the opposing surface intersecting each other generally along a particular line; and
    energy conductive means limited generally to the particular line of intersection between the opposing surfaces for cutting the body wall to create the hole into the body cavity.

2. The medical device recited in claim 1 wherein the particular line is disposed at the distal end of the tip portion.

3. The medical device recited in claim 1 wherein the particular line is a straight line.

4. The medical device recited in claim 2 wherein the shaft extends along an elongate axis and the particular line intersects the axis of the shaft.

5. The medical device recited in claim 4 wherein the particular line is perpendicular to the axis.

6. The medical device recited in claim 1 wherein each of the major surfaces has a planar configuration.

7. The medical device recited in claim 1 wherein at least one of the opposing surfaces of the tip portion intersects the outer surface of the shaft at an angle which increases from about 90° to about 180° with progressive positions proximally of the particular line.

8. The medical device recited in claim 1 wherein the energy conductive means includes an electrosurgical wire disposed along the particular line.

9. The medical device recited in claim 1 wherein the length of the particular line is generally equivalent to the diameter of the shaft.

10. A medical device for providing access across a body wall into a body cavity, comprising:
    means for creating a hole through the body wall;
    an elongate shaft included in the hole creating means and extending between a tip portion at a distal end of the shaft and a handle portion at a proximal end of the shaft, the shaft having an outer surface;
    the tip portion of the shaft defined by a pair of opposing surfaces each intersecting the outer surface of the shaft at an angle not less than 90°, the opposing surfaces intersecting each other generally along a particular line; and
    the creating means including an electrosurgical wire disposed along the particular line.

11. The medical device recited in claim 10, wherein:
    the opposing surfaces converge toward a slot at the distal end of the shaft; and
    the electrosurgical wire is disposed in the slot.

12. The medical device recited in claim 10 further comprising:
    a cannula having a working channel;
    the hole creating means disposed in the working channel of the cannula and being removable from the cannula to leave the cannula in the hole with the working channel extending into the body cavity.

13. The medical device recited in claim 10 wherein the tip portion is formed from a non-metallic, generally heat insulative material.

14. A medical device for providing access across a body wall into a body cavity, comprising:
    means for creating a hole through the body wall;
    an elongate shaft included in the hole creating means and extending between a tip portion at a distal end of the shaft and a handle portion at a proximate end of the shaft, the shaft having an outer surface;
    the tip portion of the shaft defined by a pair of opposing surfaces converging distally toward a slot; and
    energy conductive means disposed in the slot and having properties for being energized to cut the body wall.

15. The medical device recited in claim 14 wherein the opposing surfaces are generally planar in configuration.

16. The medical device recited in claim 14 wherein the opposing surfaces are generally curved in configuration.

17. The medical device recited in claim 14 wherein the opposing surfaces are disposed relative to each other at a particular angle in a range between 15° and 45°.

18. The medical device recited in claim 14 wherein the elongate shaft has an axis and the slot of the tip portion intersects the axis of the shaft.

19. The medical device recited in claim 18 wherein the slot of the tip portion is generally perpendicular to the axis of the shaft.

20. A trocar adapted for insertion through an abdominal wall between a pair of ribs, comprising:
    an elongate shaft extending along an axis between a proximal end and a distal end;
    a handle disposed at the proximal end of the shaft;
    the distal end of the shaft having the configuration of a wedge defined by a pair of surfaces which converge distally toward a line of intersection;
    energy conducting means in the form of an electrosurgical electrode disposed along the line of intersection and extending through the axis of the shaft; whereby
    the surfaces tend to separate the ribs as the trocars move generally axially through the abdominal wall between the ribs.

21. The medical device recited in claim 1 further comprising:
    insulation disposed along at least the opposing surfaces to limit exposure of the energy conductive means to the particular line of intersection.

22. The trocar recited in claim 20 wherein the shaft has a diameter and the line is generally equivalent in length to the diameter of the shaft.

23. A trocar for providing access across a body wall and into a body cavity, comprising:
    a cannula providing a working channel;
    an obturator sized and configured for removable disposition within the cannula;
    a shaft included in the obturator and having a distal tip defined by at least a first surface and a second surface which intersects the first surface along a line of intersection;
    a cutter disposed at the distal tip for cutting the body wall to permit penetration of the wall by the shaft and the cannula;

means included in the cutter for conducting energy to the distal tip of the obturator; and means for limiting exposure of the energy at the distal tip to the line of intersection.

24. The trocar recited in claim 23 wherein the shaft has an axis and the line of intersection extends transverse to the axis of the shaft.

25. The trocar recited in claim 24 wherein the conducting means comprises an electrosurgical cutter.

26. The trocar recited in claim 25 wherein the conducting means includes a wire disposed along the line of intersection.

27. The trocar recited in claim 23 wherein the first surface and the second surface are disposed in opposing relationship.

28. The trocar recited in claim 24 wherein the line of intersection forms a leading edge of the distal tip of the obturator.

29. The trocar recited in claim 28 wherein:

the shaft has the configuration of a cylinder with a diameter; and the line of intersection has a length of about the diameter of the cylinder.

30. The trocar recited in claim 24 wherein the line of intersection passes through the axis of the shaft.

31. The trocar recited in claim 23 wherein the limiting means comprises insulation disposed at the distal tip for inhibiting conduction of the energy along the first surface and the second surface.

32. A medical device for providing access across a body wall into a body cavity, comprising:

means for creating a hole through the body wall;

an elongate shaft included in the hole creating means and extending between a tip portion at a distal end of the shaft and a handle portion at a proximal end of the shaft, the shaft having an outer surface;

the tip portion of the shaft defined by a pair of opposing surfaces each intersecting the outer surface of the shaft, the opposing surfaces intersecting each other generally along a particular line; and the creating means including an electrosurgical wire disposed along the particular line.

33. A medical device for providing access across a body wall into a body cavity, comprising:

means for creating a hole through a body wall;

an elongate shaft included in the hole creating means and extending between a tip portion at a distal end of the shaft and a handle portion at a proximal end of the shaft, the shaft having an outer surface;

the tip portion of the shaft defined by a pair of opposing surfaces intersecting each other generally along a particular line, at least on of the opposing surfaces intersecting the outer surface of the shaft at an angle not less than 90°; and the creating means includes an electrosurgical conductor disposed along the particular line.

34. The medical device recited in claim 33 further comprising:

portions of the elongate shaft defining a slot along the particular line at the distal end of the shaft; and the electrosurgical conductor includes an electrosurgical wire disposed in the slot.

35. The medical device recited in claim 33 wherein at least one of the opposing surfaces has a generally planar configuration.

36. The medical device recited in claim 33 wherein the opposing surfaces are disposed relative to each other at an angle having a range between 15° and 45°.

37. The medical device recited in claim 33, wherein:

the elongate shaft has an axis; and the particular line intersects the axis of the shaft.

* * * * *